United States Patent [19]
Delmore et al.

[11] Patent Number: 5,584,446
[45] Date of Patent: Dec. 17, 1996

[54] WEB UNWINDING AND SPLICING APPARATUS

[75] Inventors: Michael D. Delmore, Mounds View; Rodney W. Hauschulz, Minnetonka; Stephen L. Bougie, Minneapolis, all of Minn.

[73] Assignee: Minnesota Mining and Manufacturing Company, St. Paul, Minn.

[21] Appl. No.: 301,237

[22] Filed: Sep. 6, 1994

[51] Int. Cl.$^6$ .................................................. B65H 19/18
[52] U.S. Cl. ........................................ 242/555; 242/559.3
[58] Field of Search ............................... 242/555, 555.1, 242/552, 559.3, 557

[56] References Cited

U.S. PATENT DOCUMENTS

| | | | |
|---|---|---|---|
| 4,170,506 | 10/1979 | Marschke | 242/552 X |
| 4,441,662 | 4/1984 | Seragnoli | 242/559.3 |
| 4,519,858 | 5/1985 | Martin | 242/552 X |
| 4,543,149 | 9/1985 | Abe et al. | 242/552 X |
| 4,951,892 | 8/1990 | Chaplin et al. | 242/557 X |
| 5,273,228 | 12/1993 | Yoshida et al. | 242/552 |
| 5,285,978 | 2/1994 | Sakano et al. | 242/559.3 X |
| 5,358,191 | 10/1994 | Lundell et al. | 242/556 |

FOREIGN PATENT DOCUMENTS

| | | | |
|---|---|---|---|
| 55-05284 | 4/1980 | Japan | 242/559.3 |
| 1427979 | 3/1976 | United Kingdom . | |

*Primary Examiner*—Daniel P. Stodola
*Assistant Examiner*—William A. Rivera
*Attorney, Agent, or Firm*—Gary L. Griswold; Walter N. Kirn; James D. Christoff

[57] ABSTRACT

A web unwinding and splicing apparatus includes two carts each supporting a plurality of web rolls, along with a first and second drive mechanism for selectively moving either cart. The carts are alternately advanced by a controller as web rolls carried by the carts are alternately depleted. The apparatus provides continuous unwinding for relatively long periods of time without operator attention.

14 Claims, 5 Drawing Sheets

WEB UNWINDING AND SPLICING APPARATUS

BACKGROUND OF THE INVENTION

1. Field of the Invention

This invention relates to automated apparatus for unwinding and splicing multiple rolls of web.

2. Description of the Related Art

A number of manufacturing processes involve webs that are initially received in roll form and are subsequently unwound from the roll for further processing. Newspapers, for example, are made by unwinding a roll of paper and then cutting the paper into sheets after a printing operation. Other examples of processes involving webs include methods for making photographic film, pressure sensitive tapes, magnetic audio, video and data storage tapes, as well as a variety of other products.

In many processes that involve unwinding of a web from a roll, the web is relatively thin and the roll represents a relatively long length of web. As a result, such web rolls are exhausted only infrequently and the unwinding process can be continued for a relatively long length of time without interruption until the roll is depleted and replaced by another roll. Paper stock for newspapers, for example, is relatively thin and a large number of newsprint sheets can be printed before the roll is exhausted.

However, other web processes involve webs that are relatively thick. As can be appreciated, a roll of relatively thick web is much shorter in length than a roll of relatively thin web for a given diameter of roll. Consequently, the rolls of thick web used in high-speed operations are quickly exhausted and must be replaced at relatively frequent intervals.

Orthopedic splinting and casting tape, such as Scotchcast™ brand and Scotchcast Plus™ brand synthetic casting tape (from 3M) is made by coating a porous knit fiberglass backing with a water curable polyurethane resin. An improved apparatus for making splinting or casting tape is described in a pending U.S. patent application entitled "Web Coating Apparatus" Ser. No 08/301,258, filed on even date herewith. However, the fiberglass backing is relatively thick (for example, about 0.5 mm) and as a result the rolls of the backing are quickly exhausted and must be frequently replaced during the coating process.

In operations involving coated webs, it is often desirable to avoid interruption of the coating process in order to help insure that the coating has a uniform thickness that does not unduly vary along the length of the web. Some fluids used to coat webs begin to cure relatively quickly when exposed to the atmosphere and may exhibit an increase in viscosity during the length of time necessary to change the roll. When the coating process is resumed with a new roll, the initial portion of the roll may have to be discarded because the change in fluid viscosity may have adversely affected the thickness, coverage or other characteristic of the coating on the initial, leading edge portion of the web that is unwound from the roll.

Web unwinding and splicing apparatus for two rolls of relatively thick web is known in the art for enabling processing of the web with fewer interruptions that would be observed for single roll unwinding apparatus. One such unwinding and splicing apparatus includes two unwind spindles located opposite one another, with a roll of web received on each spindle. When the web of one roll is exhausted, a photocell detector senses the absence of additional web from that roll and triggers a splicing mechanism. The splicing mechanism includes a pair of parallel push plates that push the trailing edge of the unwinding roll into contact with a leading edge of the standby roll. Double sided adhesive tape or other coupling means is provided to connect the webs together. An operator then places another web roll on the now-vacant spindle.

There is a continuing need in the art to decrease expenses associated with web processing operations. In this regard, there is in particular a need for an improved automated unwinding and splicing mechanism that requires less operator attention than the presently known unwinding and splicing apparatus so that the operator is free to carry out other, more productive tasks.

SUMMARY OF THE INVENTION

The present invention is directed to a web unwinding and splicing apparatus that comprises a first plurality of web rolls each having a leading edge portion and a trailing edge portion. The first plurality of web rolls is arranged in a first row. The apparatus also includes a second plurality of web rolls each having a leading edge portion and a trailing edge portion. The second plurality of web rolls is arranged in a second row in side-by-side relation to the first row. A splicing mechanism is provided for connecting the trailing edge portion of one of the web rolls of one row to the leading edge portion of one of the web rolls of the other row. The apparatus also includes a first drive mechanism for moving at least one web roll of the first row relative to the splicing mechanism and to an unwinding location upon depletion of another web roll of the first row. The apparatus also has a second drive mechanism for moving at least one web roll of the second row relative to the splicing mechanism and to an unwinding location upon depletion of another web roll of the second row.

The present invention is also directed to a method of unwinding and splicing a web that comprises the steps of unwinding web from a first web roll of a first row of web rolls, and advancing a second row of web rolls to a position wherein a first web roll of the second row is aligned with the first web roll of the first row. The method also includes the steps of splicing a trailing edge portion of the first web roll of the first row to a leading edge portion of the first web roll of the second row, and advancing the first row of web rolls to bring a second web roll of the first row to a position formerly occupied by the first web roll of the first row.

The rows of web rolls are an advantage in that a number of web rolls can be provided in each row and arranged to unwind in sequence from each row in alternate fashion. Each row, if desired, can be supported on a cart having wheels. As such, a single operator can load a number of web rolls into the apparatus in order to provide continuous, unattended unwinding and splicing of the web without interruption for a relatively long period of time.

DETAILED DESCRIPTION OF THE PREFERRED EMBODIMENTS

Figure 1:
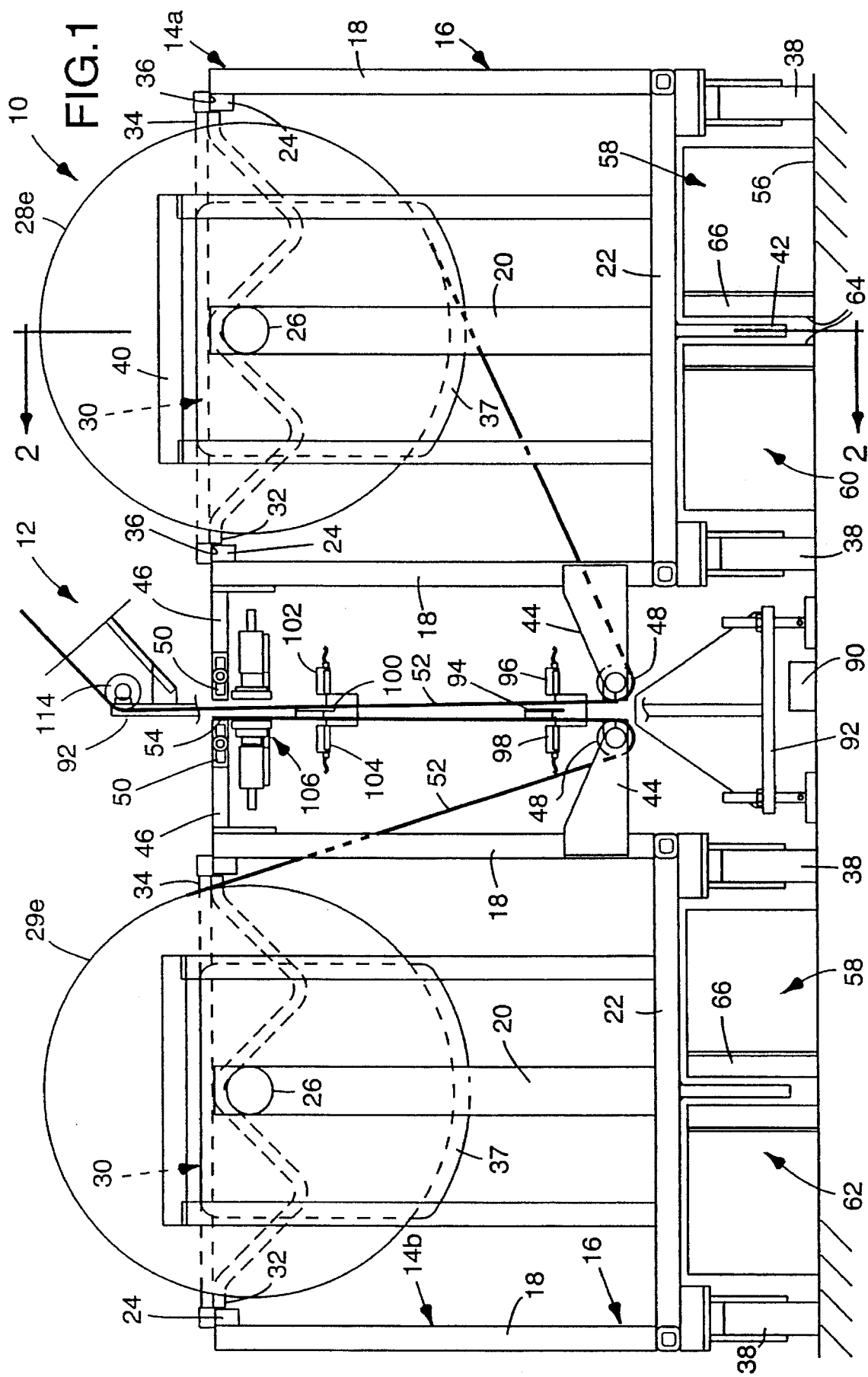
FIG. 1 is a front elevational view of a web unwinding and splicing apparatus according to one embodiment of the invention.

An unwinding and splicing apparatus for webs is designated by the numeral 10 in FIGS. 1–5. The apparatus 10 broadly includes a dual cart receiving station 12 and a pair of carts 14a, 14b (FIG. 1). Additional carts identical to the carts 14a, 14b may also be provided.

Figure 4:
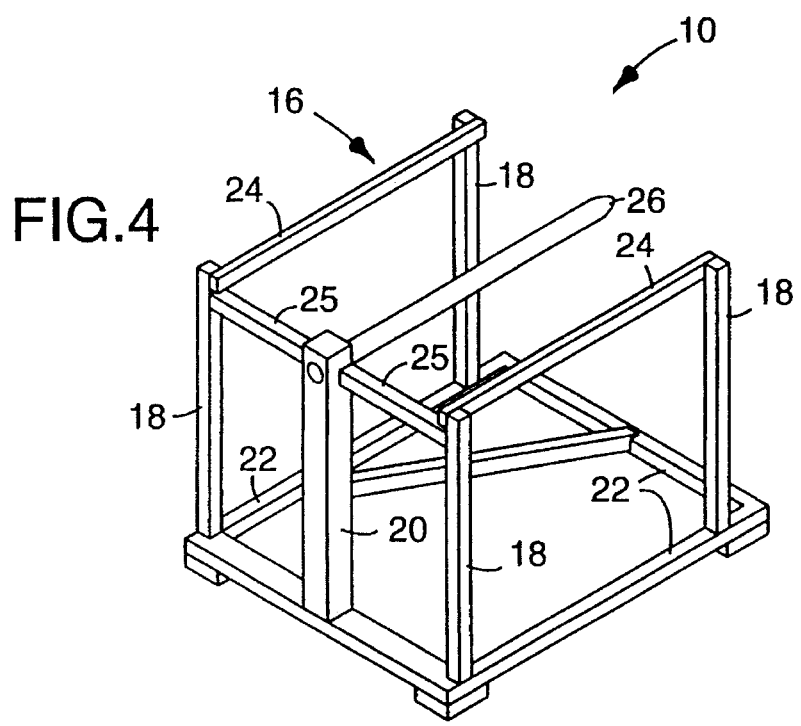
FIG. 4 is a reduced perspective view of a frame of the carts illustrated in FIGS. 1–3.

Each cart 14a, 14b includes a tubular steel frame 16 that is shown alone in FIG. 4. The frame 16 has four vertical corner posts 18 and a single vertical end post 20 that is centrally located on one end of the frame 16. Four horizontally extending lower members 22 interconnect lower ends of the corner posts 18 and the end post 20, and two parallel, horizontally extending upper side members 24 interconnect the upper ends of the posts 18 along two of the four sides of the cart 14. Two horizontally extending upper end members 25 connect upper ends of two corner posts 18 to the end post 20.

Figure 2:
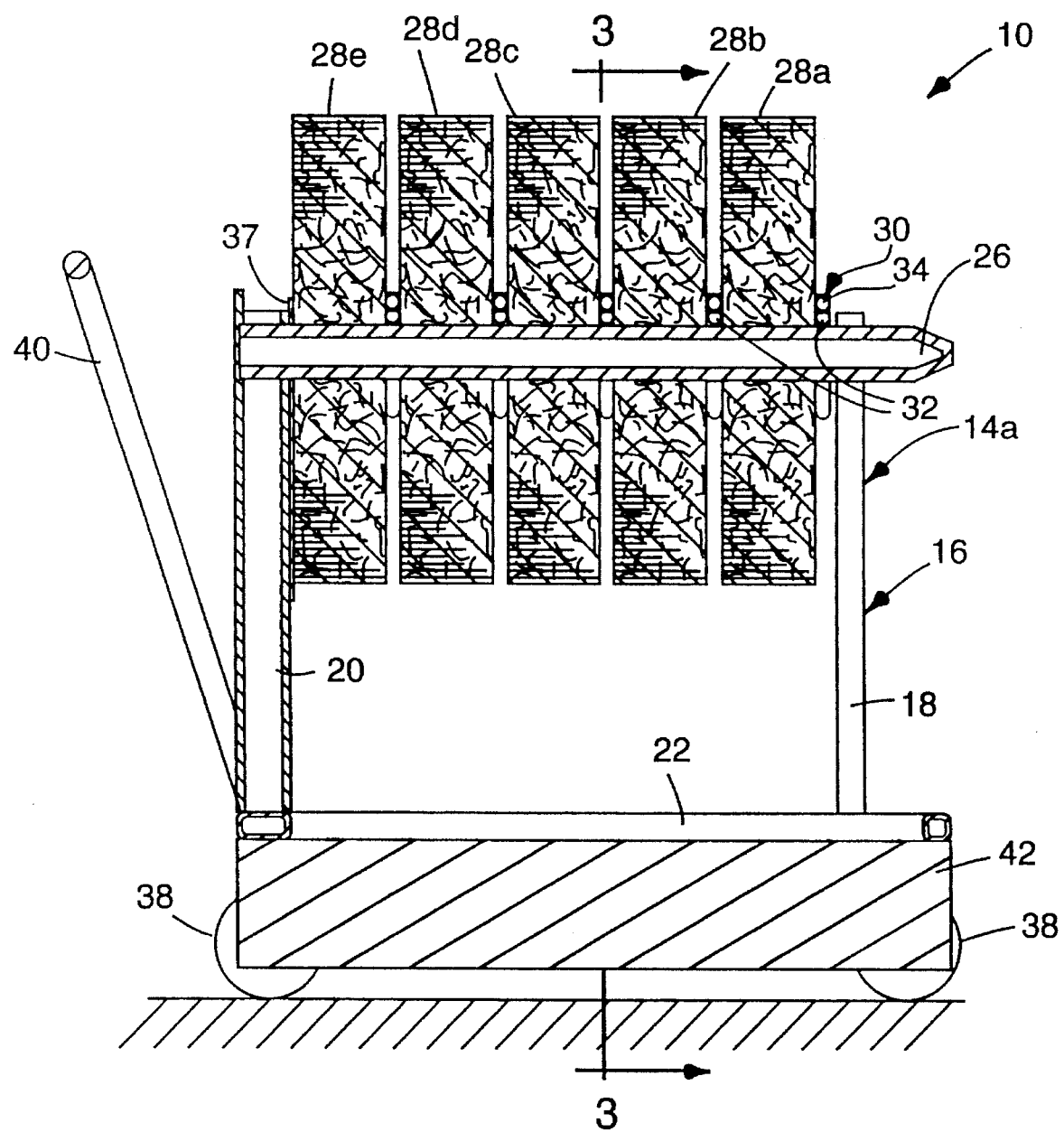
FIG. 2 is a side cross-sectional view of one of two carts of the apparatus that is shown in FIG. 1, taken along/lines 2—2 of FIG. 1 and with parts removed for clarity.

A load-bearing steel shaft 26 is fixedly secured to the upper end of the end post 20, and extends as a cantilever in a horizontal direction centrally between and parallel to the upper side members 24. The projecting end of the shaft 26 is tapered in the shape of a cone to facilitate receiving web rolls 28, 29. For exemplary purposes, FIG. 2 shows the cart 14a receiving and supporting a first row of five web rolls numbered 28a–e. Also for exemplary purposes, the cart 14b (shown in FIG. 1) receives and supports a second row having an equal number of web rolls, such as web rolls 29a–e (only roll 29e is shown in the drawings). The first and second rows are straight and parallel to each other.

Figure 3:
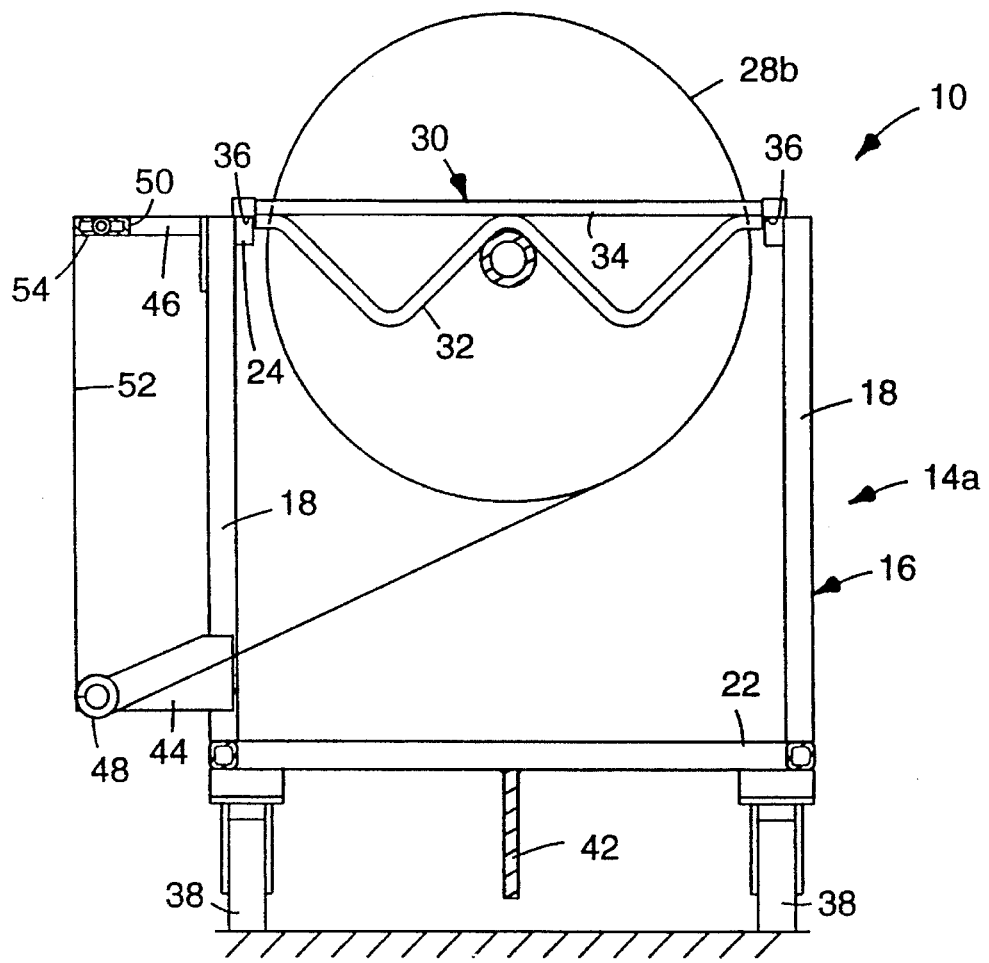
FIG. 3 is a cross-sectional view of the cart illustrated in FIG. 2, taken along lines 3—3 of FIG. 2.

Five stainless steel spacers 30 are removably received on the two upper side members 24 of each cart 14a, 14b. The spacers 30 are located between each web roll 28, 29 as well as on the side of the web roll 28, 29 nearest the conical free end of the shaft 26. As illustrated in FIG. 3, each spacer 30 includes a lower, generally W-shaped bar 32 and a straight upper bar 34 that is secured to both ends and the middle of the bar 32. Each end of the upper bar 34 includes a portion that projects past the ends of the lower bar 32, and a magnet 36 is secured to the underside of each projecting portion of the upper bar 34.

The magnets 36 detachably connect each spacer 30 to the frame 16 at any location along the length of the upper side members 24. As a consequence, each cart 14 can accommodate web rolls having a width that is different than the width of the web rolls 28 illustrated in FIG. 2. If, for example, each web roll is relatively narrow, additional spacers 30 may be provided so that the carts 14 can receive more than five web rolls. The spacers 30 keep the web rolls 28, 29 spaced from each other, and also apply tension to the web rolls 28, 29 while unwinding. A back plate 37 (shown in part by dashed lines in FIG. 1) is located between the end post 20 and each of the web rolls 28e, 29e.

A presently preferred use of the unwinding and splicing apparatus 10 is in the manufacture of orthopedic splinting or casting tape, such as Scotchcast™ brand or Scotchcast Plus™ brand casting tape (from 3). A suitable web to serve as a backing for such tape is an annealed porous knit fiberglass material such as is described in U.S. Pat. No. 4,609,578, the disclosure of which is incorporated by reference herein. Preferably, the web rolls 28, 29 that are made of such material do not include a core, and instead the web material that surrounds the central hole of each web roll 28, 29 is in direct contact with the shaft 26.

If desired, a braking system can be added to apply pressure to the web rolls 28, 29 while unwinding. The braking system could comprise a roller mounted on a swingable arm and located to apply drag on the unwinding roll 28, 29 so that the unwinding web remains in tension.

Each cart 14 includes four casters located below each corner post 18, and each caster includes a wheel 38. A handle 40, having an inverted, generally U-shaped configuration, is fixed to one of the lower frame members 22 and straddles the end post 20. A guide rail 42 is fixed to two of the lower frame members 22. The guide rail 42 extends in a vertical plane and is elongated in a horizontal direction parallel to and beneath the shaft 26 from one end of the frame 16 to the other.

The cart 14a has two lower brackets 44 fixed to two of the corner posts 18, along with two horizontally extending arms 46 fixed to the upper end of the same corner posts 18. FIGS. 1 and 3 illustrate one of the two brackets 44 and one of the two arms 46. A stationary, horizontally extending cylindrical guide rod 48 extends between the lower brackets 44. A rectangular, horizontally extending bar 50 is coupled by a pivot to the outer end of each arm 46. As shown in FIG. 1, cart 14b has similar lower brackets 44, arms 46, guide rod 48 and bar 50 located on an opposite side of the cart 14b.

A leading edge portion 52 of each web roll 28, 29 extends downwardly and about the guide rod 48 of the corresponding cart 14a, 14b, and then upwardly in a vertical direction for releasable connection with the bar 50. A length of hook section 54 of a hook and loop fastener (such as Scotchmate™ hook and loop fastener from 3M) is secured along the length of the bar 50 for mating connection with the end of the leading edge web portion 52. The bar 50 is pivoted about its horizontal pivot axis in order to facilitate connection of the end of the leading edge web portion 52 to the hook section 54.

Figure 5:
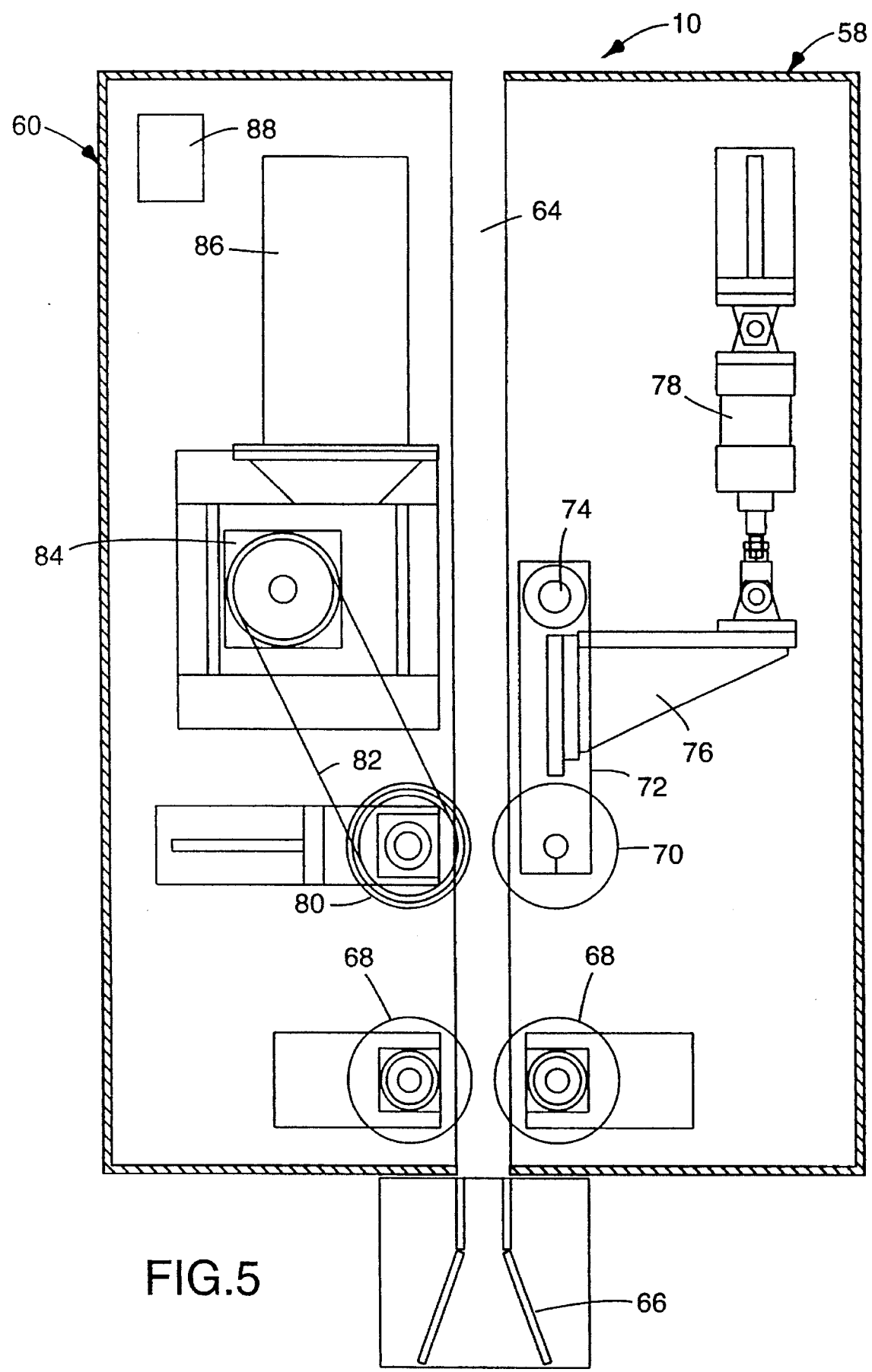
FIG. 5 is a plan view of one of two drive mechanisms of the apparatus shown in FIG. 1 for advancing one of the carts such as the cart shown in FIGS. 2–3.

The apparatus 10 includes a flat horizontal platform 56 (FIG. 1) that supports a housing 58 of a first drive mechanism 60 and a second drive mechanism 62. A horizontal view of the first drive mechanism 60 is illustrated in FIG. 5 with the top of its housing 58 removed to show various elements. The second drive mechanism 62 is identical to the first drive mechanism 60 and as such a detailed description of the second drive mechanism 62 need not be provided.

The housing 58 of the first drive mechanism 60 has slots in its top and two end walls to present a guide channel 64 that extends from one end of the housing 58 to the other. A funnel-shaped entrance 66 of the guide channel 64 is located next to the slot in one end of the housing 58 for guiding the movement of the cart 14 as the guide rail 42 is moved toward and into the guide channel 64. FIG. 1 illustrates the orientation of the guide rail 42 when the cart 14 is pushed onto the platform 56 and the guide rail 42 is received in the guide channel 64.

As shown in FIG. 5, the first drive mechanism 60 includes a pair of guide rollers 68 that are rotatable about respective vertical axes. The guide rollers 68 are located on opposite sides of the channel 64 and are spaced apart a distance slightly larger than the width of the guide rail 42.

A urethane covered idler roller 70 is rotatable about a vertical shaft that is fixed to one end of a horizontally extending arm 72. The arm 72 is mounted on a pivot 74 for swinging movement in a horizontal arc. A bracket 76 is fixed to the arm 72 and is coupled by an adjustable-length connector to a piston rod of a pneumatic double-acting piston and cylinder assembly 78. The cylinder of the piston and cylinder assembly 78 is connected by a bracket to the platform 56.

A urethane covered drive roller 80 is positioned next to the idler roller 70 and is fixed to a rotatable vertical shaft that is connected to a bearing block secured to the platform 56. A toothed belt 82 is connected to a pulley that is secured to the shaft connected to the drive roller 80, and the toothed belt 82 also extends about a pulley mounted on a vertical output shaft of a gear reducing right angle drive 84. A servomotor 86 (such as Model DXM-340W from Emerson Electronic Motor Controls) has an output shaft that is coupled to an input shaft of the right angle drive 84. As an option, the belt 82 and pulleys may be replaced by a chain drive and sprockets.

The servomotor 86 is electrically connected to a servodrive 88 (such as Model No. DXA-340, PCM-5 ratio controller from Emerson Electronic Motor Controls). In turn, the servodrive 88 of the first drive mechanism as well as the servodrive of the second drive mechanism 62 are connected to a single programmable logic controller 90 that is shown schematically in FIG. 1. The controller 90 is also electrically coupled to solenoid operated air valves (not shown) that are interposed in tubing connected to a source of pressurized air and the cylinders of the piston and cylinder assembly 78 of the first and second drive mechanisms 60, 62. Preferably, proximity sensors (not shown) are connected to the controller 90 and are strategically located to confirm the arrival and positions of the carts 14a, 14b.

An upright stand 92 is fixed to the platform 56. A central portion of the stand 92 has been broken away in FIG. 1 to better illustrate the leading edge portions 52 of the webs 28, 29. The stand 92 carries a first combination light source and detector 96 and a second combination light source and detector 98. The first and second light source and detectors 96, 98 are positioned to direct light toward, and sense reflected light from, a double-sided reflector 94. The stand 92 also carries a third combination light source and detector 102 and a fourth combination light source and detector 104 that direct light toward, and sense reflected light from, a double-sided reflector 100. All of the combination light source and detectors 96, 98, 102, 104 are electrically connected to the controller 90 and optionally include a diffusing lens to avoid sensing light passing through interstices in the webs 28, 29.

Figure 6:
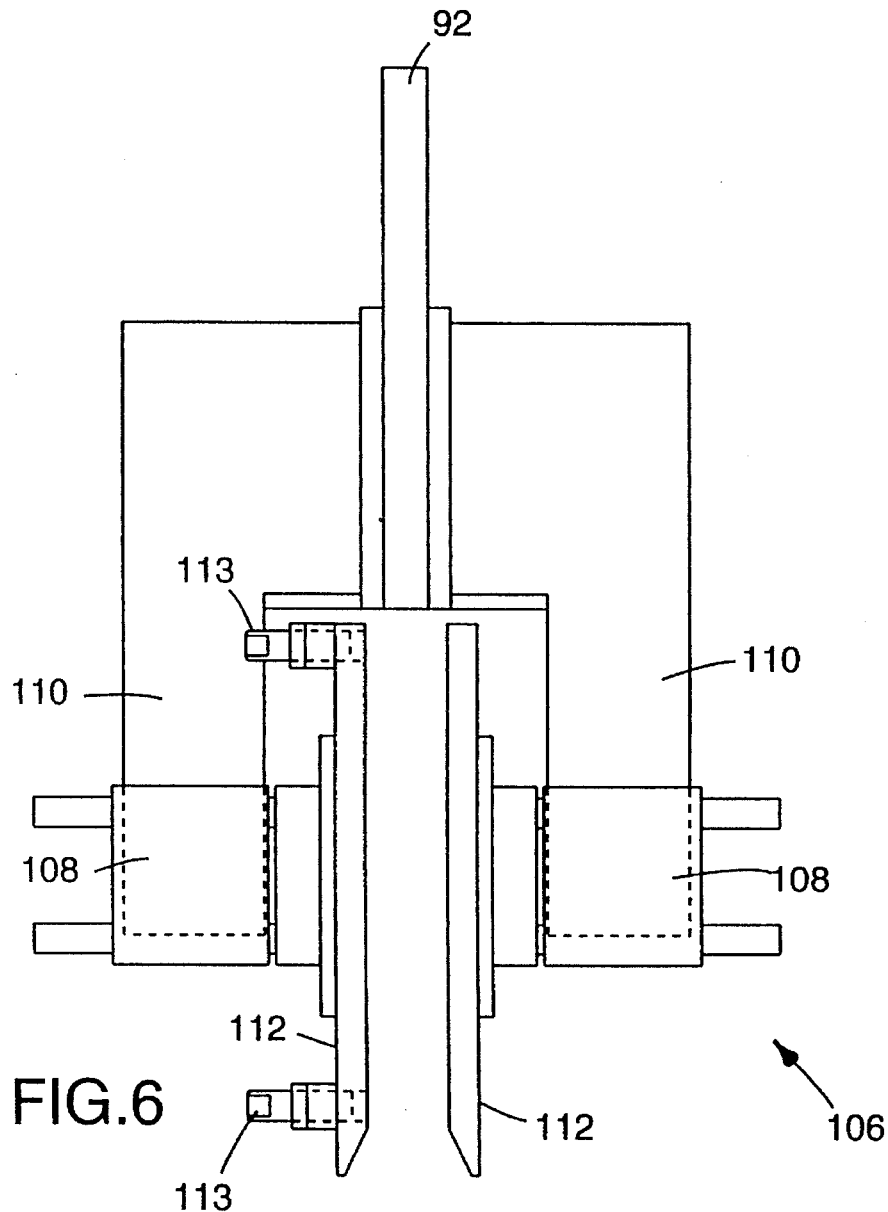
FIG. 6 is an enlarged plan view of a splicing mechanism of the apparatus depicted in FIG. 1.
Figure 7:
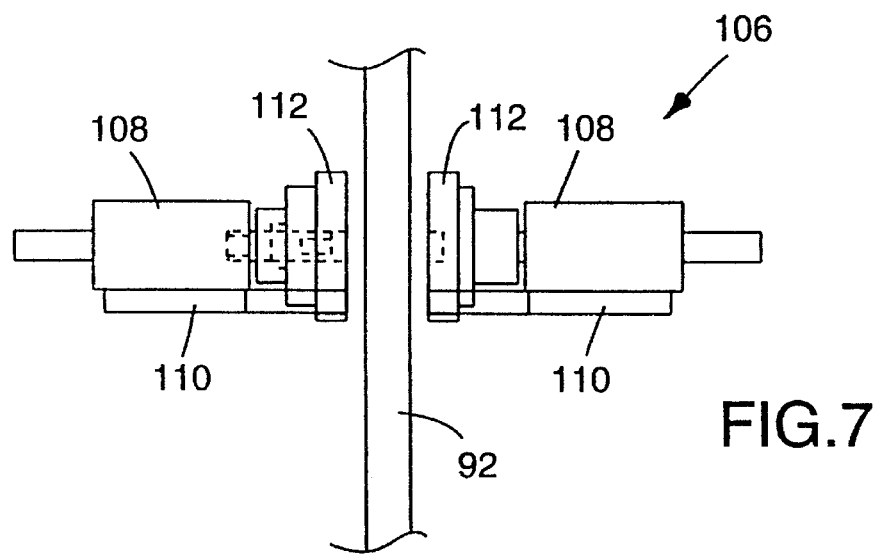
FIG. 7 is a front elevational view of the splicing mechanism shown in FIG. 6.

A splicing mechanism 106 of the apparatus 10 is illustrated in FIG. 1, and is shown in enlarged view in FIGS. 6 and 7. The splicing mechanism 106 includes a pair of pneumatic, double-acting dual piston and cylinder assemblies 108 that are secured to respective L-shaped brackets 110 connected to the stand 92. The dual sliding pistons of the piston and cylinder assemblies 108 are connected to push plates 112 having a beveled front end as shown, for example, in FIG. 6. A pair of adjustable stops 113 are mounted on one of the push plates 112 to limit the distance the plates 112 can advance toward each other.

The piston and cylinder assemblies 108 are connected by tubing to the aforementioned source of pressurized air. Solenoid operated air valves are coupled to the tubing and are electrically connected to the controller 90.

The upper end of the stand 92 is coupled to a web guide roller 114 (see FIG. 1) that is rotatable about a horizontal axis. From the roller 114, the web is advanced to a processing operation, such as a coating or cutting operation. When the web is used in the manufacture of orthopedic splinting or casting tape, the downstream operation preferably includes the coating apparatus that is described in the aforementioned U.S. patent application Ser. No. 08/301,258 entitled "Web Coating Apparatus". Preferably, the controller 90 is also utilized for controlling the operation of the coating apparatus.

In use, the operator first prepares the carts 14a, 14b by loading the web rolls 28, 29 (and the spacers 30) onto the carts 14a, 14b. The leading edge of each web roll 28, 29 is affixed to the hook sections 54 of the hook and loop fasteners. The bar 50 is then pivoted to an upright orientation, and a section of double-sided pressure sensitive adhesive tape is placed on the leading edge portion 52 of each web roll 28, 29 at a location next to the now-vertical side of the bar 50. The bar 50 is pivoted back to its orientation illustrated in FIGS. 1 and 3 and as a result the adhesive tape is then located at a height corresponding to the height of the splicing mechanism 106.

Next, the operator activates the apparatus by depressing a "start" button electrically connected to the controller 90. The controller 90, through the servodrives 88, energizes the servomotor 86 of each drive mechanism 60, 62 to initiate rotation of the drive roller 80. In addition, the controller 90 extends the piston of the piston and cylinder assembly 78 of each drive mechanism 60, 62 to cause the arm 72 to swing about the pivot 74 and move the idler roller 70 closer toward, but still spaced from, the corresponding drive roller 80.

The operator then pushes the first cart 14a toward the first drive mechanism 60 such that the guide rail 42 moves into the entrance 66 and the guide channel 64. Once the drive roller 80 contacts the forward end of the guide rail 42, the drive roller 80 advances the cart 14a without further assistance from the operator. The piston and cylinder assembly 78 causes the idler roller 70 to push the guide rail 42 firmly against the drive roller 80 to facilitate advancement of the cart 14a along a first path without slippage.

As the cart 14a advances, the leading edge portion 52 of the first web roll 28a enters the space directly opposite the third combination light source and detector 102. As soon as the leading edge portion 52 of the web roll 28a blocks passage of reflected light to the third combination light source and detector 102, the controller 90 de-energizes the servomotor 86 of the first drive mechanism 60 to stop further advancement of the cart 14a. The second cart 14b is placed in the second drive mechanism 62 by the operator and is advanced in the same manner and along a second path that is located in side-by-side, spaced apart relation to the first path until the leading edge portion 52 of the first web roll 29a of the second cart 14b enters the space directly opposite the fourth combination light source and detector 104. Once the leading edge portion 52 of the web roll 29a blocks passage of reflected light to the fourth combination light source and detector 104, the controller 90 de-energizes the servomotor 86 of the second drive mechanism 62. At that time, the first web roll 28a of the first cart 14a is in a first unwinding location and is directly across from the first web roll 29a of the second cart 14b (which is in a second unwinding location that is spaced from the first unwinding location).

The operator then guides the leading edge portion 52 of the first web roll 28a of cart 14a about the web guide roller 114 and then to the downstream operation. The downstream operation preferably includes a metering roller or some other device to pull the web and unwind the web roll 28a.

Once the web roll 28a of the cart 14a is depleted, a trailing end of the web roll 28a moves past the first combination light source and detector 96 and the reflector 94. Once the light source and detector 96 senses light from the reflector 94, the controller 90 activates the splicing mechanism 106 to cause the push plates 112 to move toward each other. As the push plates 112 meet, the leading edge portion of the web roll 29a of the second cart 14b is detached from the hook section connected to the bar of the cart. In addition, as the leading edge portion of the web roll 29a engages the trailing edge portion of the web roll 28a, the section of double-sided pressure sensitive adhesive tape previously connected to the leading edge portion of the web roll 29a next to the push plates 112 engages the trailing edge portion of the web roll 28a, to thereafter couple the leading edge portion and the trailing edge portion together. After a short interval (e.g., such as 0.2 seconds) the controller 90 reverses air pressure to the piston and cylinder assembly 108 to cause the push plates 112 to move apart and back to their initial, retracted orientations.

As soon as the controller 90 has caused the push plates 112 to retract, the controller 90 through the servodrive 88 energizes the servomotor 86 of the first drive mechanism 60 to advance the first cart 14a and thereby advance the first row of web rolls 28. Advancement of the first cart 14a continues until such time as a leading edge portion of the second web roll 28b occupies the space previously occupied by the web roll 28a. Once the third combination light source and detector 102 senses the leading edge portion 52 of the web roll 28b, the controller 90 de-energizes the servomotor 86 to interrupt further advancement of the cart 14a and the first row of web rolls 28.

The foregoing operation is then repeated in similar manner as the first web roll 29a of the second cart 14b is unwound. Once the trailing edge of the first web roll 29a of the second cart 14b moves past the second combination light source and detector 98, the splicing mechanism 106 is again triggered to cause the trailing edge portion of the web roll 29a of the second cart 14b to connect to the leading edge portion of the second web roll 28b of the first cart 14a. The second cart 14b (and thus the second row of web rolls 29) is then advanced by the second drive mechanism 62 until such time as the fourth combination light source and detector 104 senses the leading edge portion of the second web roll 29b.

Thereafter, operation of the apparatus 10 continues by unwinding web rolls alternately from the rows of web rolls 28, 29 of the carts 14a, 14b respectively. Once all of the web rolls 28a–e in the first row (i.e., on the first cart 14a) are depleted, the first drive mechanism 60 advances the cart 14a to such an extent that the cart 14a is expelled from the end of the housing 58 opposite the entrance 66 since the third light detector 102 fails to detect the presence of additional web. The operator then advances another cart into the entrance 66 for continuing the unwinding operation without interruption of web movement as the web unwinds from the web roll 29e. Likewise, once all of the web rolls 29a–e in the second row (i.e., on the second cart 14b) have been depleted, the cart 14b is ejected past the housing of the second drive mechanism 62 and the operator then feeds a newly loaded cart toward the second drive mechanism 62.

As can be appreciated, the drive roller 80 and the idler roller 70 provide a means for releasably coupling to and driving the movement of the first cart 14a once the first cart 14a has been moved on wheels 38 toward a position of contact with the first drive mechanism 60, and the first drive mechanism 60 advances the first cart 14a toward the end of the housing 58 opposite the entrance 66 upon depletion of the web rolls 28a–28e in order to uncouple the first cart 14a from the first drive mechanism 60.

A number of modifications and additions to the invention described above may be apparent to those skilled in the art. For example, a single motor may be used for both drive mechanisms with an electric clutch or other means to distribute motive power alternately to the carts 14a, 14b. As another example, the vertical location of the reflector 94 and the combination light source and detectors 96, 98 may be altered by use of an adjustable supporting structure so that the time between detection of the trailing end of a web roll and activation of the splicing mechanism may be varied in accordance with the speed of web movement or other parameter. Accordingly, the invention should not be limited to the embodiments described in detail above, but should only be limited by a fair scope of the claims that follow and their equivalents.

We claim:

1. A web unwinding and splicing apparatus comprising:

a first cart having wheels, said first cart carrying a first plurality of web rolls each having a leading edge portion and a trailing edge portion, said first plurality of web rolls being arranged in a first row;

a second cart having wheels, said second cart carrying a second plurality of web rolls each having a leading edge portion and a trailing edge portion, said second plurality of web rolls being arranged in a second row in side-by-side relation to said first row;

a splicing mechanism for connecting the trailing edge portion of one of said web rolls of one of said rows to the leading edge portion of one of said web rolls of the other of said rows;

a first drive mechanism for advancing said first cart including at least one web roll of said first row relative to said splicing mechanism along a first path in a certain direction for moving said at least one web roll of said first row to a first unwinding location upon depletion of another web roll of said first row; and a second drive mechanism for advancing said second cart including at least one web roll of said second row relative to said splicing mechanism along a second path and for moving said at least one web roll of said second row to a second unwinding location upon depletion of another web roll of said second row, wherein said first unwinding location is spaced from said second unwinding location and wherein said second path is located in side-by-side, spaced apart relation to said first path, said first drive mechanism including means for releasably coupling to and driving the movement of said first cart once said first cart has been moved on said wheels of said first cart toward a position of contact with said first drive mechanism, said first drive mechanism advancing said first cart in said certain direction upon depletion of said first plurality of web rolls in order to enable said first cart to be uncoupled from said first drive mechanism.

2. The apparatus of claim 1, wherein said first cart and said second cart each include a rail, and wherein said first drive mechanism and said second drive mechanism each include a drive roller releasably engaging said rail of said first cart and said second cart respectively.

3. The apparatus of claim 1, wherein each of said carts include a shaft having a certain length for supporting said web rolls and spacers for placement between adjacent pairs of web rolls, and wherein said spacers are releasably connectable to said cart at any one of a number of locations along the length of said shaft.

4. The apparatus of claim 1, wherein said first cart and said second cart each include a rail, and wherein said first drive mechanism and said second drive mechanism each include a drive roller and an idler roller for contact with opposite sides of said rail of said first cart and said second cart respectively.

5. The apparatus of claim 4, wherein said idler roller of each of said first drive mechanism and said second drive mechanism is selectively movable in directions toward said rail of said first cart and said second cart respectively and in directions away from said rail of said first cart and said second cart respectively.

6. The apparatus of claim 1, wherein said rows are straight.

7. The apparatus of claim 1, wherein said rows are parallel to each other.

8. The apparatus of claim 1, wherein said second drive mechanism includes means for releasably coupling to and driving the movement of said second cart once said second cart has been moved on said wheels of said second cart toward a position of contact with said second drive mechanism.

9. A method of unwinding and splicing a web comprising the steps of:

coupling a first cart to a first drive mechanism;

unwinding web from a first web roll of a first row of web rolls carried by the first cart;

advancing a second cart carrying a second row of web rolls along a certain path and to a position wherein a first web roll of the second row is aligned with the first web roll of the first row;

splicing a trailing edge portion of the first web roll of the first row to a leading edge portion of the first web roll of the second row;

advancing the first row of web rolls along a path that is in side-by-side, spaced apart relation to said certain path to bring a second web roll of the first row to a position formerly occupied by the first web roll of the first row; and uncoupling the first cart from the first drive mechanism once all of the web rolls of the first row have been depleted.

10. The method of claim 9, wherein said step of advancing the first cart includes the step of rolling the first cart on wheels.

11. The method of claim 9, wherein said step of advancing the first cart includes the step of rotating a drive roller of the first drive mechanism.

12. The method of claim 9 and including the step of applying tension to the first web roll of the first row of web rolls while unwinding the first web roll of the first row of web rolls.

13. The method of claim 9 and including the step of moving the first cart toward the first drive mechanism before said step of coupling the first cart to the first drive mechanism.

14. The method of claim 9 and including the step of releasably coupling the second cart to a second drive mechanism.

* * * * *